US00PP24878P2

(12) United States Plant Patent
Sills et al.

(10) Patent No.: US PP24,878 P2
(45) Date of Patent: Sep. 16, 2014

(54) BLACKBERRY PLANT NAMED 'DRISBLACKSEVEN'

(50) Latin Name: ***Rubus* L. subgenus *Rubus***
Varietal Denomination: DrisBlackSeven

(71) Applicant: Driscoll Strawberry Associaates, Inc., Watsonville, CA (US)

(72) Inventors: Gavin R. Sills, Gilroy, CA (US); Jose Maurilio Rodríguez Mesa, Michoacan (MX); Jorge Rodriguez Alcazar, Texcoco (MX); Andrea M. Pabon, Gilroy, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/986,030

(22) Filed: Mar. 25, 2013

(51) Int. Cl.
*A01H 5/08* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

PP17,162 P3 * 10/2006 Clark et al. ..... Plt./203

* cited by examiner

*Primary Examiner* — June Hwu
*Assistant Examiner* — Keith Robinson
(74) *Attorney, Agent, or Firm* — Jondle Plant Sciences Division of Swanson & Bratschun, L.L.C.

(57) ABSTRACT

A new and distinct variety of blackberry plant named 'DrisBlackSeven', particularly characterized by high yielding, self fruitful plants, early fruit ripening, and long conical shaped berries with sweet flavor is disclosed.

2 Drawing Sheets

Genus and species: *Rubus* L. subgenus *Rubus*.
Variety denomination: 'DrisBlackSeven'.

BACKGROUND OF THE NEW PLANT

The present invention relates to a new and distinct blackberry cultivar designated 'DrisBlackSeven' and botanically known as *Rubus* L. subgenus *Rubus*. This new blackberry variety was identified in Ventura County, Calif. in March 2006 and originated from a cross between the proprietary female parent blackberry plant 'BJ111-2' (unpatented) and the proprietary male parent blackberry plant 'BH917-6' (unpatented). A single plant was selected for asexual propagation via tissue culture and root cuttings in Santa Cruz, Calif. in 2006.

'DrisBlackSeven' underwent further testing in La Isla Grande, Mexico for 3 years (2010-2012). The present invention has been found to retain its distinctive characteristics through successive asexual propagations via tissue culture and root cuttings.

Plant Breeder's Rights for this variety have not been applied for. 'DrisBlackSeven' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in La Isla Grande, Mexico.

1. High yielding, self fruitful plants;
2. Early fruit ripening; and
3. Long conical shaped berries with sweet flavor.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from 3-year old plants.

Figure 1:
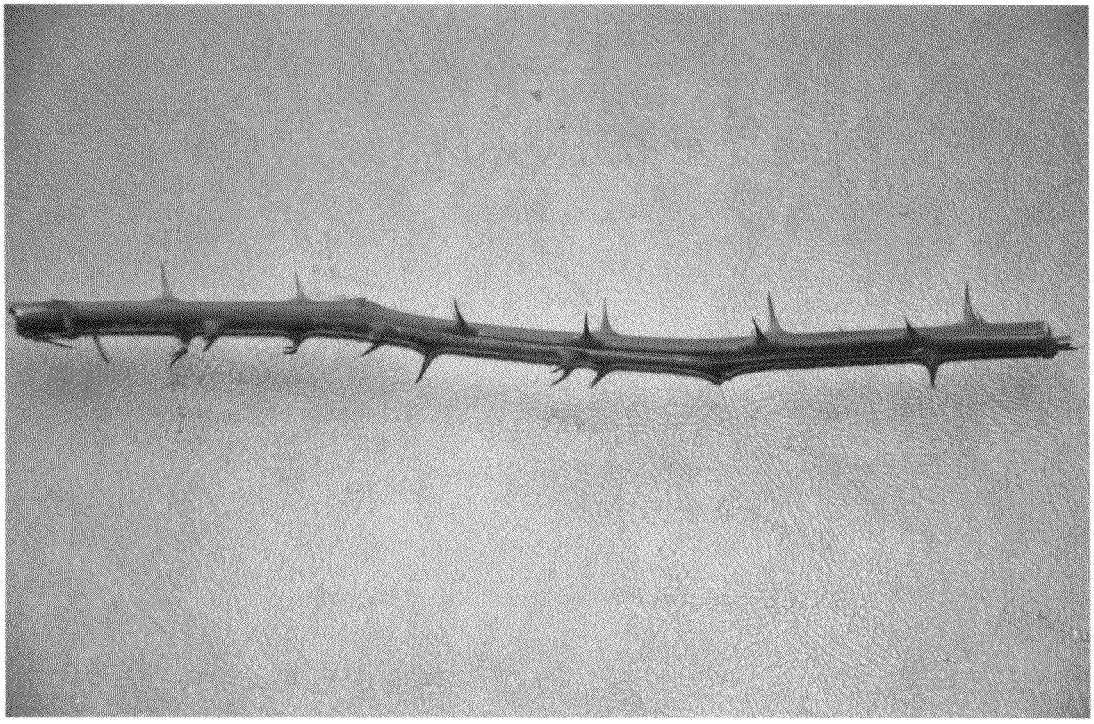
Figure 2:
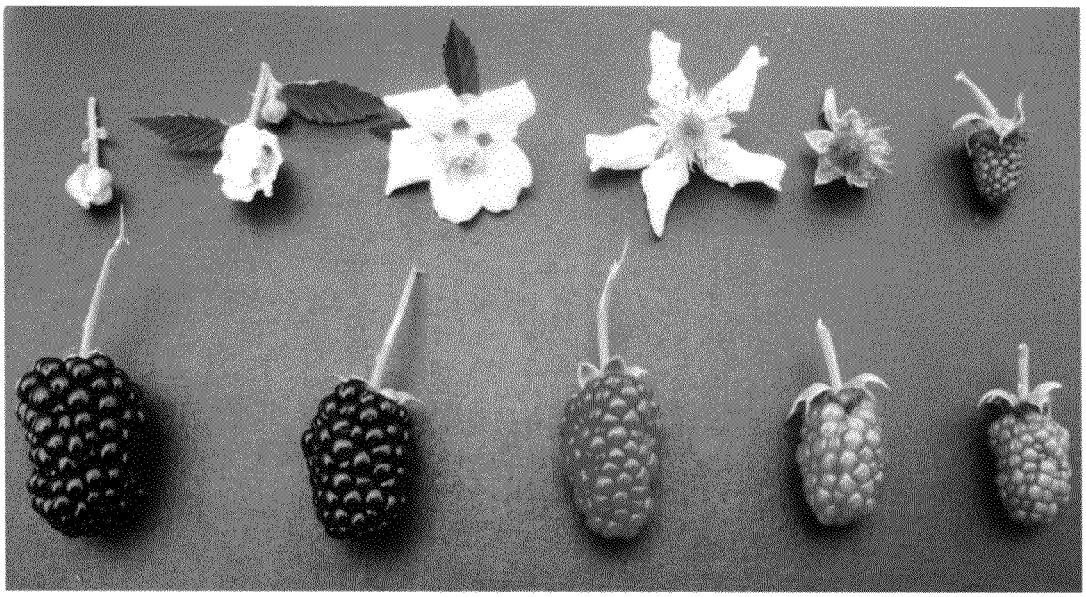
Figure 3:
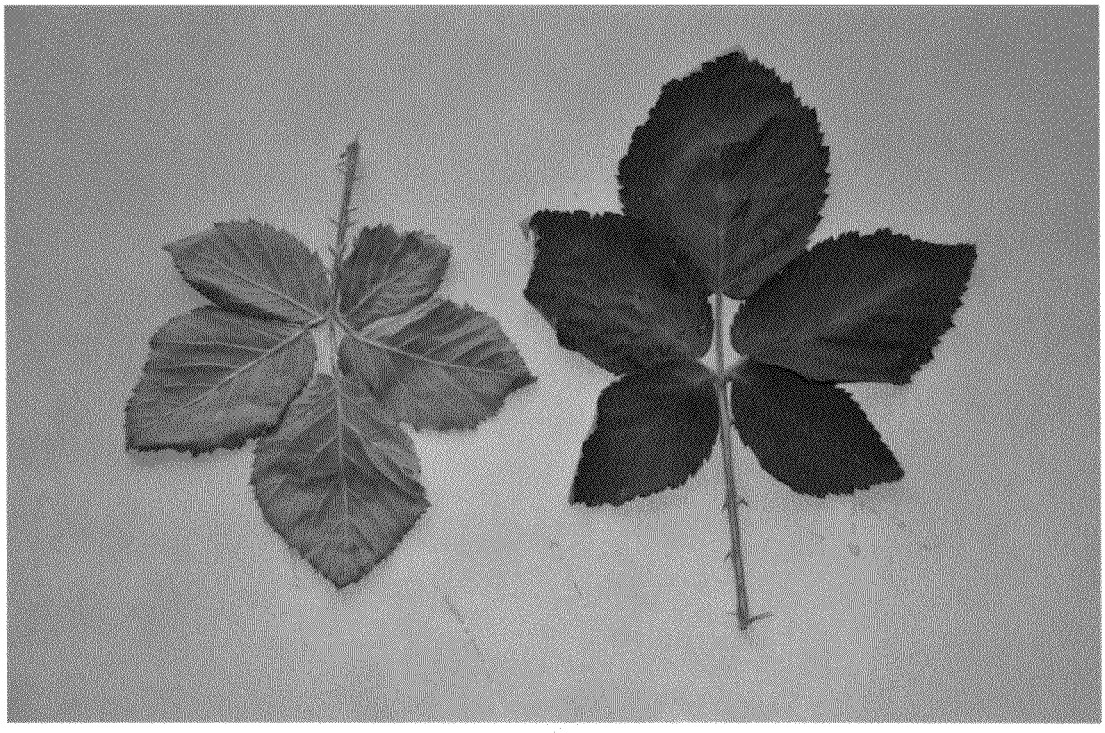

FIG. 1 shows a section of a young cane with spines.
FIG. 2 shows the flowers and the fruit at various stages.
FIG. 3 shows the upper and lower surfaces of the leaves.

DESCRIPTION OF THE NEW VARIETY

The following detailed descriptions set forth the distinctive characteristics of 'DrisBlackSeven'. The data which define these characteristics is based on observations taken in La Isla Grande, Mexico from 2010 to 2012. This description is in accordance with UPOV terminology. Color designations, color descriptions, and other phenotypical descriptions may deviate from the stated values and descriptions depending upon variation in environmental, seasonal, climatic and cultural conditions. 'DrisBlackSeven' has not been observed under all possible environmental conditions. The botanical description of 'DrisBlackSeven' was taken from 3-year old plants. Color terminology follows The Royal Horticultural Society Colour Chart, London (R.H.S.) (2007 edition). Descriptive terminology is from the *Plant Identification Terminology, An Illustrated Glossary* $2^{nd}$ edition, by James G. Harris and Melinda Woolf Harris, unless where otherwise defined.

DETAILED BOTANICAL DESCRIPTION

Classification:

*Family*.—Rosaceae.

*Botanical*.—*Rubus* L. subgenus *Rubus*.

*Common name*.—Blackberry.

*Variety name*.—'DrisBlackSeven'.

Parentage:

*Female parent*.—Proprietary blackberry plant named 'BJ111-2' (unpatented).

*Male parent*.—Proprietary blackberry plant named 'BH917-6' (unpatented).

Plant:

*Vigor*.—Medium.

*Growth habit*.—Upright to semi-upright.

*Productivity*.—High yield.

*Propagation*.—Tissue culture and root cuttings.

*Self-fruitfulness*.—Self-fruitful.

*Time of bud burst*.—Early; late February to mid-March.

Canes:

*Fruiting lateral length* (4$^{th}$ *lateral from tip*).—Short; 17.4 cm.

*Number of fruit per lateral*.—8.0.

*Fruiting on current year's cane*.—Present.

*Cane internodal distance*.—6.7 cm.

*Number of new canes during flowering*.—Many; 1 to 2.

*New cane strength* (*observed full-grown shoot after picking*).—Moderately vigorous.

*Glaucosity observed on full-grown shoot after picking*.—Strong.

*Spines*.—Size: Medium; 8.0 to 10.0 mm. Color: RHS 151A (Medium yellow-green). Density on central third of cane: Moderately dense. Texture: Medium. Attitude of apex in relation to cane: Downwards.

*Young shoots*.—Quantity: Many; 3 to 5. Time of emergence from soil: Early. Anthocyanin coloration (during rapid growth): Medium; RHS 77C (Light purple). Intensity of green color: Medium; RHS 141C (Medium green). Number of glandular hairs: Many.

*Dormant cane*.—Length: Medium. Diameter (in central third): Medium; 10.0 to 12.0 mm. Cross section (from mid cane observed at end of first growing season): Rounded to angular. Color: RHS 138B (Medium green). Number of branches: Many; 3 to 4. Distribution of branches: Over whole length. Anthocyanin coloration: Absent to very weak; RHS 138B (Medium green). Spines: Present. Number of spines: Many.

Leaves:

*Type*.—Palmate.

*Predominant number of leaflets*.—Five.

*Overlapping or relative position of lateral leaflets*.—Overlapping.

*Color*.—Upper surface: Dark; RHS 137B (Dark green). Lower surface: Medium; RHS 138A (Medium green).

*Glossiness of upper side*.—Medium.

*Cross section profile*.—Convex (margins rolled backwards).

*Leaflets*.—Shape: Ovate. Margin: Doubly serrate. Depth of incisions: Medium; 2.0 to 3.0 mm. Type of incision margin: Bi-serrate. Apex: Complex. Base: Obtuse. Rachis length between terminal leaflet and adjacent lateral leaflet: 28.4 mm.

*Lateral leaflet* (*basal pair*).—Length: 6.48 cm. Width: 4.37 cm. Length/width ratio: 1.5.

*Terminal leaflet*.—Length: Long; 7.34 cm. Width: Medium; 5.81 cm. Length/width ratio: 1.3. Lobing: Absent. Undulation of margin (rippling of margin): Medium. Blistering between veins (rugosity): Medium. Shape: Ovate. Tip: Truncate. Base: Obtuse. Margin: Doubly serrate. Cross-section: V-shaped.

*Petiole*.—Length: 25.3 mm. Diameter: 1.6 mm. Pigmentation: Upper surface: Medium; RHS 177B (Medium greyed-orange). Lower surface: RHS 138B (Medium green).

*Stipule*.—Size: Medium. Orientation: Reflexed.

Inflorescence:

*Time of beginning of flowering on previous year's cane*.—Early.

*Time of beginning of flowering on current year's cane*.—Early.

*Flower diameter*.—Medium; 4.07 cm.

*Flower number* (at 3$^{rd}$ *node from tip of lateral*).—6.

*Petal*.—Length: 2.04 cm. Width: 1.42 cm. Length/width ratio: 1.4. Color: RHS 62D (Light red-purple).

*Pedicel*.—Length: 2.27 cm. Diameter: 1.74 mm.

Fruit:

*Time of ripening on previous year's cane*.—Early.

*Time of ripening on current year's cane*.—Early.

*Harvest interval*.—Early October through mid June.

*Color*.—Immature: RHS 138B (Medium green). Maturing: RHS N34A (Dark orange-red). Mature: RHS 202A (Black).

*Glossiness*.—Medium.

*Shape in longitudinal section*.—Long conical.

*Size*.—Medium.

*Length*.—Medium; 3.47 cm.

*Width*.—Narrow; 1.79 cm.

*Ratio of length to width*.—1.9 (longer than broad).

*Weight* (*g/fruit*).—6.2 g.

*Soluble solids* (%) (*in Brix*).—9.7.

*Titratable acidity*: (% *as citric acid*).—0.89.

*Seed weight* (*g/seed*).—0.3.

*Number of druplets/fruit*.—Medium; 101.

*Size of druplet*.—Small.

*Firmness*.—Medium.

*Yield*.—High.

*Market use*.—Fresh market.

Disease, Pest, and Stress Resistance:

*Botrytis fruit rot*.—Resistant.

*Powdery mildew*.—Resistant.

*Verticillium wilt*.—Resistant.

*Tetranychus urticae*.—Moderately susceptible.

*Drought*.—Moderately resistant.

*High temperatures*.—Resistant.

*Wind*.—Moderately resistant.

*Water logging*.—Resistant.

COMPARISON WITH PARENTAL AND COMMERCIAL VARIETIES

'DrisBlackSeven' differs from the proprietary female parent 'BJ111-2' (unpatented) in that 'DrisBlackSeven' has spines and medium size fruit, whereas 'BJ111-2' is spineless and has small to medium size fruit.

'DrisBlackSeven' differs from the proprietary male parent 'BH917-6' (unpatented) in that 'DrisBlackSeven' has smaller fruit and earlier fruit production than 'BH917-6'.

'DrisBlackSeven' differs from the commercial variety 'Sleeping Beauty' (U.S. Plant Pat. No. 13,758) in that 'Dris- BlackSeven' has high productivity, medium size flowers, a short fruiting lateral length and long conical shaped fruit in longitudinal section, whereas 'Sleeping Beauty' has moderately high productivity, large flowers, a medium-long fruiting lateral length, and elliptical shaped fruit in longitudinal section.

We claim:

1. A new and distinct variety of blackberry plant named 'DrisBlackSeven' as described and shown herein.

* * * * *